US008618291B2

(12) United States Patent
Schils et al.

(10) Patent No.: US 8,618,291 B2
(45) Date of Patent: *Dec. 31, 2013

(54) PROCESS FOR PREPARING 4-[(1,6-DIHYDRO-6-OXO-2-PYRIMIDINYL)AMINO]BENZONITRILE

(75) Inventors: Didier Philippe Robert Schils, Loupoigne (BE); Alfred Elisabeth Stappers, Oud-Turnhout (BE)

(73) Assignee: Tibotec Pharmaceuticals Ltd., Eastgate Village, Eastgate—Little Island, Cork (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/325,621

(22) Filed: Dec. 14, 2011

(65) Prior Publication Data

US 2012/0083606 A1  Apr. 5, 2012

Related U.S. Application Data

(63) Continuation of application No. 11/913,200, filed as application No. PCT/EP2006/062606 on May 24, 2006, now Pat. No. 8,101,752.

(60) Provisional application No. 60/685,993, filed on May 31, 2005.

(30) Foreign Application Priority Data

May 26, 2005 (EP) .................................. 05104531

(51) Int. Cl.
*C07D 239/47* (2006.01)

(52) U.S. Cl.
USPC ........................................................ 544/321

(58) Field of Classification Search
USPC .......................................................... 544/321
See application file for complete search history.

(56) References Cited

U.S. PATENT DOCUMENTS

| 5,223,505 | A | 6/1993 | Hargreaves et al. |
| 6,878,717 | B2 | 4/2005 | De Corte et al. |
| 7,034,019 | B2 | 4/2006 | Kukla et al. |
| 7,037,917 | B2 | 5/2006 | De Corte et al. |
| 7,125,879 | B2 * | 10/2006 | Guillemont et al. .......... 514/256 |
| 7,241,458 | B1 | 7/2007 | Verreck et al. |
| 7,399,856 | B2 | 7/2008 | Schils et al. |
| 7,514,445 | B2 | 4/2009 | Freyne et al. |
| 7,563,922 | B2 | 7/2009 | Schils et al. |
| 7,705,149 | B2 | 4/2010 | Edwards et al. |
| 8,101,752 | B2 * | 1/2012 | Schils et al. ................. 544/321 |
| 2005/0004125 | A1 | 1/2005 | Freyne et al. |

FOREIGN PATENT DOCUMENTS

| RU | 2037483 | 6/1995 |
| RU | 2108329 | 4/1998 |
| WO | WO 91/01298 | 2/1991 |
| WO | WO 99/50250 | 10/1999 |
| WO | WO 00/27825 | 5/2000 |
| WO | WO 03/016306 | 2/2003 |

OTHER PUBLICATIONS

Spychala, J. "A Facile Preparation of N2-Arylisocytosines", Synthetic Communications, 27 (11), 1943-1949 (1997). XP009062618.
Krapcho, A. Paul, et al. "Synthetic Applications and Mechanism Studies of the Decarbalkoxylations of Geminal Diesters and Related Systems Effected in $Me_2SO$ by Water and/or by Water with Added Salts", J. Org. Chemistry, vol. 43, No. 1, (1978), pp. 138-147.
Krapcho, A. Paul, et al. Synthetic Applications of Dealkoxycarbonylations of Malonate Esters, β-Keto Esters, α-Cyano Esters and Related Compounds in Dipolar Aprotic Media-Part 1, Synthesis, Issue 10, vol. 1982, pp. 805-822.
Krapcho, A. Paul, et al. Synthetic Applications of Dealkoxycarbonylations of Malonate Esters, β-Keto Esters, α-Cyano Esters and Related Compounds in Dipolar Aprotic Media-Part 2, Synthesis, Issue 11, vol. 1982, pp. 893-914.

* cited by examiner

*Primary Examiner* — Venkataraman Balasubramanian
(74) *Attorney, Agent, or Firm* — Rajiv S. Shah; Kirk Baumeister

(57) ABSTRACT

This invention relates to a process for preparing 4-[(1,6-dihydro-6-oxo-2-pyrimidinyl)-amino]benzonitrile (I) starting from a 4-oxo-1,6-dihydro-pyrimidinylcarboxylic acid ester (II) or starting from a guanidine derivative which is reacted with an alkoxy-methylene malonic acid ester to an ester (II) which is converted to (I), which reaction sequence may be a one-pot procedure.

17 Claims, No Drawings

PROCESS FOR PREPARING 4-[(1,6-DIHYDRO-6-OXO-2-PYRIMIDINYL) AMINO]BENZONITRILE

CROSS REFERENCE TO RELATED APPLICATIONS

This application is a continuation of U.S. application Ser. No. 11/913,200 filed Oct. 31, 2007 now U.S. Pat. No. 8,101,752 which is the National Stage application under 35 U.S.C. §371 of PCT/EP06/62606, filed May 24, 2006, which claims priority to U.S. Provisional Application Ser. No. 60/685,993 filed May 31, 2005, the contents of all of which are incorporated herein by reference in their entirety.

FIELD OF THE INVENTION

This invention relates to a process for preparing 4-[(1,6-dihydro-6-oxo-2-pyrimidinyl)-amino]benzonitrile (I) starting from a 4-oxo-1,6-dihydro-pyrimidinylcarboxylic acid ester (II) or starting from a guanidine derivative which is reacted with an alkoxy-methylene malonic acid ester to an ester (II) which is converted to (I), which reaction sequence may be a one-pot procedure.

BACKGROUND OF THE INVENTION

The virus causing the acquired immunodeficiency syndrome (AIDS) is generally known as the human immunodeficiency virus (HIV). The spread of HIV has caused and continues to cause serious health problems throughout the world. A number of HIV inhibitory drugs have been developed that currently are used to combat the virus. These drugs have proven out to be effective in suppressing the virus, in particular when used in combination therapy. However no therapy is capable of completely eliminating the virus from the body.

Several classes of HIV inhibitors at present are available and new ones are being explored. One such class is that of that of the non-nucleoside reverse transcriptase inhibitors (NNRTIs). This class comprises a number of drugs that are used in anti-HIV therapy while other NNRTIs are in various stages of development. One of these is the compound 4-[[4-[[4-(2-cyanoethenyl)-2,6-dimethylphenyl]-amino]-2-pyrimidinyl]-amino]-benzonitrile, also known as TMC278. This compound, its properties as well as a number of synthetic approaches for its preparation have been described in WO-03/16306. TMC278, which currently is in clinical development, not only shows pronounced activity against wild type virus, but also against many mutated variants.

Consequently there is a need for producing larger quantities of this active ingredient based on processes that provide the product in high yield and with a high degree of purity. A synthesis strategy that has been developed to prepare this compound involves coupling (E)-4-amino-3,5-dimethylcinnamonitrile (B) with anilinopyrimidine (C) to obtain TMC278 as outlined in the following reaction scheme, wherein the compound TMC278 is represented by formula (A).

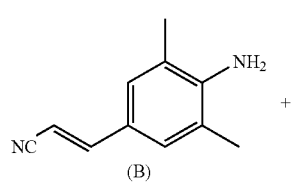

(B)

+

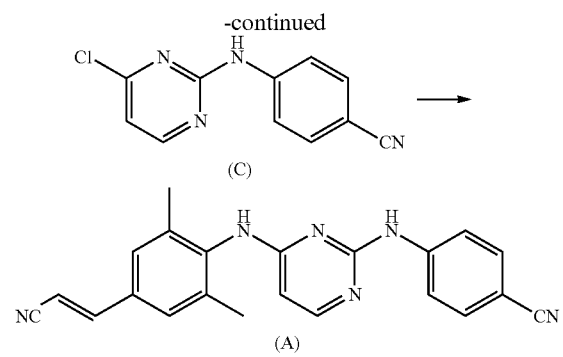

(C)

(A)

The preparation of intermediate (B) has been described in WO-04/016581 as comprising coupling 4-iodo-2,6-dimethylaniline (D) (X=I) with acrylonitrile in the presence of palladium on charcoal, sodium acetate as a base and dimethylacetamide as a solvent.

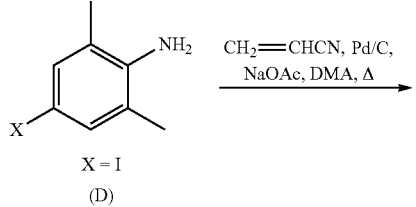

(D)

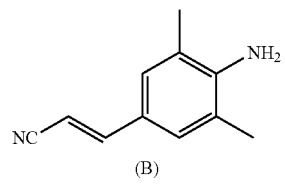

(B)

The preparation of intermediate (C) on the other hand has been described in WO-03/16306 as comprising a halogenation reaction of 4-oxo-1,6-dihydro-pyrimidine (I), in particular with POCl₃.

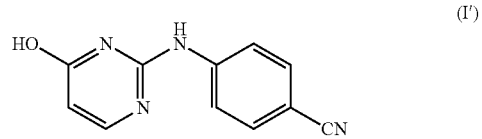 [SMILES: N#Cc1ccc(Nc2nccc(O)n2)cc1]

Compound (I), which sometimes is represented by its tautomeric form (I'):

(I')

can be prepared following the procedure described in Synthetic Communications, 27 (11), 1943-1949 (1997):

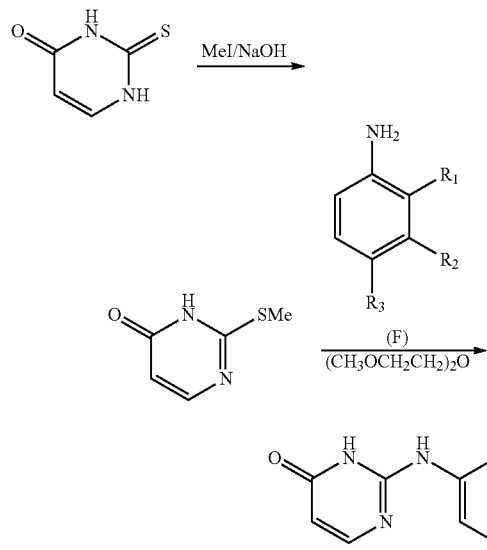

The reaction of (E) with (F) results in the liberation of methyl mercaptane, a toxic and extremely odorous compound, which can be smelled at concentrations as low as 2 ppb. Complete removal of this mercaptane therefore is a requirement, posing a very difficult purification challenge. This makes this process impractical for large-scale production.

WO-00/27825 discloses at p.14 the synthesis of structural analogs of compound (I) bearing a Y substituent in 5-position and a Q substituent in 6-position of the pyrimidine moiety. The group Y in these structural analogs cannot be hydrogen and in particular is halogen and is never a carboxyl ester group as required in the process of the present invention. Moreover the synthesis disclosed in this reference lacks a decarboxylation step, which is essential in the process of the present invention.

Although the above mentioned prior art process via intermediates (E) and (F) may be useful for preparing small quantities of the desired product of formula (I), there is a need for a process that can be scaled up for the production of multi-kilogram and larger quantities, that is reproducible, is economical and through which the end product is obtained in high yield and with a high degree of purity. Providing such a process is an object of the present invention.

SUMMARY OF THE INVENTION

The present invention concerns a process for preparing an intermediate in the synthesis of TMC278, in particular it concerns a process for preparing a compound of formula:

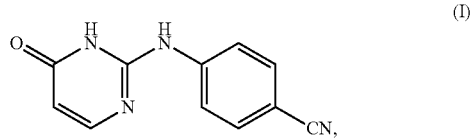 [SMILES: N#Cc1ccc(Nc2nccc(=O)[nH]2)cc1]

wherein the compound of formula (I) is prepared by dealkoxycarbonylating a 4-oxo-1,6-dihydro-pyrimidinyl carboxylic acid ester of formula (II):

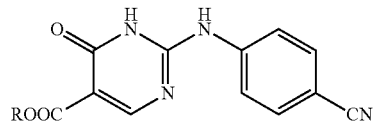

wherein R is $C_{1-4}$alkyl.

In a further aspect, the invention concerns a process for preparing the compound of formula (I), as specified above, wherein the compound of formula (I) is prepared by condensing a guanidine derivative of formula (III) with an alkoxymethylene malonic acid ester of formula (IV), thus obtaining an intermediate (II), as specified above, which is dealkoxycarboxylated to obtain the desired end product of formula (I), as outlined in the following reaction scheme wherein each R, independently from the other radicals R, represents $C_{1-4}$alkyl:

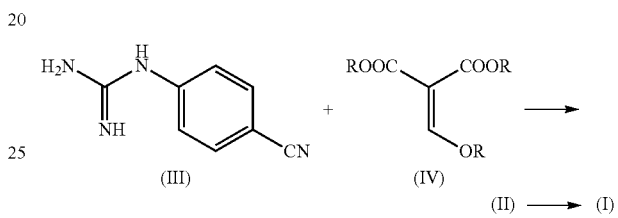

In one embodiment, the conversion from (III) over (II) to obtain (I) is conducted in a one-pot procedure, without isolation of intermediate (II).

DETAILED DESCRIPTION OF THE INVENTION

TMC278 occurs in stereoisomeric forms, more in particular as E- and Z-isomeric forms. The preferred form of TMC278 is the E-isomer, i.e. (E)-4-[[4-[[4-(2-cyano-ethenyl)-2,6-dimethylphenyl]-amino]-2-pyrimidinyl]-amino]-benzonitrile (hereinafter called E-TMC278). The other isomer is the Z-isomer of TMC278, i.e. (Z)-4-[[4-[[4-(2-cyanoethenyl)-2,6-dimethylphenyl]-amino]-2-pyrimidinyl]-amino]-benzonitrile (which is referred to as Z-TMC278). Whenever mention is made herein to 'TMC278', the E-form is referred to, as well as any mixture of both forms that predominantly contains the E-form, e.g. at least 80%, in particular at least 90%, more in particular at least 95%, or even at least 99% of the E-form.

Compound (I) occurs in two tautomeric forms, namely those having structure (I) and (I'). For the purposes of this disclosure and claims, structures (I) and (I') should be considered as referring to the same chemical entity and both (I) and (I') should be considered as equivalent representations of this chemical entity.

As used herein, each radical R, independently from the others, represents $C_{1-4}$alkyl. The latter defines straight or branched chain saturated hydrocarbon radicals having from 1 to 4 carbon atoms such as methyl, ethyl, 1-propyl, 2-propyl, 1-butyl, 2-butyl, 2-methyl-1-propyl, 2-methyl-2-propyl. Of particular interest are $C_{1-4}$alkyl radicals wherein the carbon atom linked to the oxygen atom forms a methylene group. $C_{1-4}$alkyl preferably is a linear $C_{1-4}$alkyl (i.e. n.$C_{1-4}$alkyl such as n.propyl). More preferably each R independently is selected from methyl and ethyl. In one embodiment all R radicals are methyl, in another embodiment all R radicals are ethyl.

The conversion from (II) to (I) involves a dealkoxycarbonylation reaction with expulsion of $CO_2$. This reaction may be performed under the conditions described by Krapcho (see e.g. Krapcho et al., J. Org. Chem., 43, 138-147 (1978); Krapcho, Synthesis, 805-822, 893-914 (1982)).

In preferred embodiments, the reaction is conducted in the presence of a suitable salt of formula MX wherein M is a metal, an ammonium or substituted ammonium cation, and X is an anion having nucleophilic properties. M for example may be an alkali metal or earth alkaline metal ion e.g. a lithium, sodium, potassium, magnesium, calcium ion. Ammonium or substituted ammonium comprises, for example, $NH_4^+$, quaternary ammonium wherein the ammonium is substituted with alkyl (preferably $C_{1-4}$alkyl) and/or benzyl, e.g. tetra n.butylammonium, trimethyl benzyl ammonium, tributyl benzylammonium. Suitable X groups are the halide anions, in particular chloride and bromide; carboxylic acid anions, in particular $C_{1-4}$alkylcarboxylates, such as acetate or propionate; cyanides. Preferred are chloride, bromide, acetate and cyanide, acetate being particularly preferred. Of particular interest are the alkali metal salts of the above mentioned anions. Particular examples of salts MX that can be used are sodium cyanide, sodium acetate, sodium chloride, sodium bromide, potassium cyanide, potassium acetate, potassium chloride, potassium bromide, tetra n.butylammonium acetate, tetra n.butylammonium cyanide.

The conversion from (II) to (I) may be conducted in a suitable reaction-inert solvent, preferred solvents being the dipolar aprotic solvents such as dimethylformamide (DMF), dimethylacetamide (DMA), hexamethylphosphoric acid triamide (HMPT), N-methylpyrrolidone (NMP), dimethylsulfoxide (DMSO), acetonitrile and the like, including mixtures thereof. A particularly preferred solvent is NMP.

In a preferred mode of carrying out the process of this invention, the dealkoxycarbonylation reaction of (II) is carried out in NMP in the presence of an acetate salt, e.g. potassium acetate or, in particular, sodium acetate. This particular mode of carrying out a dealkoxycarboxylation reaction has hitherto not been described in the literature and has proved out to be very effective.

The dealkoxycarboxylation reaction may be conducted at elevated temperature, for example at a temperature in the range of about 130° C. to the reflux temperature of the reaction mixture, in particular in the range of about 140° C. to about 170° C., more in particular in particular in the range of about 140° C. to about 160° C. Preferably the dealkoxycarboxylation reaction is conducted over a certain period of time, such as from about 24-120 hours, or in particular from about 24-48 hours, or more in particular from about 24-36 hours. In one embodiment, the reaction is conducted at increased pressure thereby allowing even higher temperatures such as up to about 200° C. or by microwave heating. This allows the reaction time to be reduced to time periods of several hours e.g. about 2-6 hours.

In particular the preferred reaction conditions mentioned above, i.e. conducting the reaction in NMP with an acetate salt such as sodium or potassium acetate, allow the use of microwave heating or the use of increased pressure and higher temperatures as mentioned above, thereby reducing the reaction time while still obtaining the desired end product in high yield and purity.

At the end of the dealkoxycarbonylation an acid may be added to the reaction mixture. The acid preferably is added when the dealkoxycarbonylation step is completed. The acid that is added preferably an organic acid such as an alkylcarbonic acid, in particular a $C_{1-4}$alkylcarbonic acid, e.g. acetic or propionic acid. Without being bound to theory, it is assumed that the addition of acid decomposes the pyrimidinyloxide salt of formula

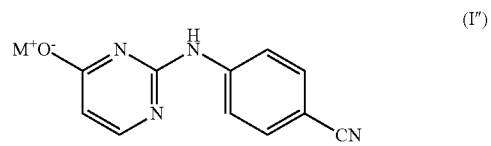

wherein M is as defined above, to obtain the desired end product of formula (I). The acid preferably is added to the reaction mixture being at increased temperature such as in the range of about 100° C. to about 150° C., in particular of about 120° C. to about 140° C.

The yield may further be optimized by taking the resulting product up in a lower alkanol such as a $C_{1-4}$alkanol, preferably ethanol, and heating, preferably refluxing the alkanol mixture for a period which may range from a couple of minutes to a few hours, e.g. from about 10 min to about 3 hours, in particular from about 30 min to about 2 hours.

The intermediate of formula (II) may be prepared by condensing a guanidine derivative of formula (III) with an alkoxymethylene malonic acid ester of formula (IV). This reaction may be conducted in a suitable solvent, preferably a dipolar aprotic solvent such as any of the solvents mentioned above in relation to the reaction of (II) to (I). A preferred solvent is NMP. Preferred esters of formula (IV) are methoxy- and ethoxymethylene malonic acid dimethyl and diethyl esters. The methyl derivative often is referred to as dimethyl (methoxymethylene)malonate. The reaction of (III) with (IV) preferably is conducted at elevated temperature e.g. at a temperature which is in the range of about 70° C. to about 130° C., in particular of about 80° C. to about 120° C. The mixture is allowed to react for a period if tune sufficient to complete the reaction, which time period may vary e.g. from about 30 min to about 3 hours, in particular from about 1 to 2 hours.

A particular aspect of this invention concerns a process for preparing the compound of formula (I) starting from intermediates (III) and (IV) to obtain the intermediate (II) and subsequent dealkoxycarbonylation of (II) to obtain compound (I). Each of the steps of this process may be conducted in the same solvent or solvent mixture and using the same reaction conditions as described above for the preparation of end product (I) starting from (II) and the reaction of (III) with (IV).

In one embodiment, this process is conducted in a one-pot procedure, without isolation of intermediate (II). The one pot procedure can be done in the same solvent. A particular solvent suitable for this one-pot process is NMP. This process variant offers the possibility to synthesize compound (I) in a quick, simple and straightforward manner.

In one embodiment, the salt used in the dealkoxycarboxylation is added to the reaction mixture used in the condensation of (III) with (IV), i.e. at the beginning of the reaction procedure. This has the practical advantage that the salt does not have to be added to the reactor in the middle of the reaction procedure, i.e. after the termination of the reaction of (III) with (IV). It moreover has been found that the salt does not interfere in the condensation reaction of (III) with (IV). A particular salt suitable for this one-pot process is an acetate salt such as an alkali metal acetate, e.g. sodium acetate.

An additional feature of the present invention comprises the fact that the intermediates of formula (II) are novel compounds. Therefore, in a further aspect, the invention provides a compound of formula (II) having the chemical structure as specified above, wherein R is as defined above, as well as the acid-addition salts thereof. The term "acid-addition salts" as mentioned herein is meant to comprise any stable salts, which the intermediates of formula (II) are able to form. Preferred are the pharmaceutically acceptable acid-addition salts, which are the non-toxic acid addition salt forms. The salts can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzene-sulfonic, cyclohexanesulfamic, 2-hydroxybenzoic, 4-amino-2-hydroxybenzoic and the like acids. Conversely the salt form can be converted by treatment with alkali into the free base form. The term addition salts is also meant to include the hydrates or solvates which the compounds of formula (I) are able to form, including, e.g. the alcoholates such as methanolates or ethanolates.

The process of the present invention allows scaling up for the production of multi-kilogram and larger quantities, and is reproducible and economical. The desired end product is obtained in high yield and with a high degree of purity. Further advantages that may be mentioned are the availability of starting materials and reagents that may be commercially available or easy to prepare.

The intermediate of formula (I) can also be used in the synthesis of TMC120, i.e. 4-[[4-[(2,4,6-trimethylphenyl)amino]-2-pyrimidinyl]amino]benzonitrile, which is a further NNRTI that is currently being developed as a microbicidal in the prevention of transmission of HIV infection as disclosed in WO-03/094920. TMC120, its synthesis and properties have been described in WO-99/50250. To prepare TMC120, compound (I) is converted to compound (C) as described above and the latter compound (C) is reacted with 2,4,6-trimethylaniline thus obtaining the compound TMC 120. Similar analogs of TMC278 and TMC 120 can be obtained in a similar manner.

All references cited in this specification are incorporated herein in their entirety.

The following examples are meant to illustrate the present invention and not to limit it thereto.

EXAMPLES

Example 1

A mixture of 64 g (0.4 mol) of (4-cyanophenyl)guanidine, 98.4 g (1.2 mol) sodium acetate and 76.6 g (0.44 mol) dimethyl(methoxymethylene)malonate in 600 ml N-methylpyrrolidinone (NMP) was heated to 100° C. and stirred for 1 hour at that temperature. 64.8 ml of demineralized water was added and the reaction mixture was further heated to reflux temperature. About 100 ml of the solvent was evaporated until the temperature of the reaction mixture reached the range of 155° C. to 160° C. Subsequently the reaction mixture was refluxed during 30 hours. The whole is allowed to cool to 20-25° C. and 25 g filtration aid was added. After stirring the mixture for 1 hour at 20-25° C., the precipitate was filtered off and washed with 40 ml of NMP. The solvent was distilled off under vacuum and the residue was heated to 120° C. 300 ml acetic acid was added dropwise (during 15 minutes) to the heated residue while keeping the temperature at 130° C. After addition of the acetic acid, the mixture was heated to 150° C. and stirred at that temperature for 15 minutes. Subsequently, the mixture was allowed to cool to 20-25° C. The formed precipitate was filtered off and washed with ethanol (1×200 ml and 1×80 ml). 400 ml ethanol was added to the washed precipitate and this mixture was heated and refluxed for 1 hour. After cooling to 20-25° C., the precipitate was filtered off, washed with 100 ml ethanol and dried at 50° C. under vacuum during 16 hours. Yield: 65.6 g of 4-[(1,4-dihydro-4-oxo-2-pyrimidinyl)-amino]benzonitrile.

Example 2

A mixture of 64 g (0.4 mol) of (4-cyanophenyl)guanidine, 98.4 g (1.2 mol) sodium acetate and 76.6 g (0.44 mol) diethyl (ethoxymethylene)malonate in 600 ml N-methyl-pyrrolidinone (NMP) was heated to 100° C. and stirred for 1 hour at that temperature. 81 ml of demineralized water was added and the reaction mixture was further heated to reflux temperature. About 120 ml of the solvent was evaporated until the temperature of the reaction mixture reached the range of 155° C. to 160° C. Subsequently the reaction mixture was refluxed during 72 hours. The whole is allowed to cool to 20-25° C. and 25 g filtration aid was added. After stirring the mixture for 1 hour at 20-25° C., the precipitate was filtered off and washed with 50 ml of NMP. The solvent was distilled off under vacuum and the residue was heated to 130° C. 375 ml acetic acid was added dropwise (during 15 minutes) to the heated residue while keeping the temperature at 130° C. After addition of the acetic acid, the mixture was heated to 150° C. and stirred at that temperature for 15 minutes. Subsequently, the mixture was allowed to cool to 20-25° C. The formed precipitate was filtered off and washed with ethanol (1×250 ml and 1×100 ml). 500 ml ethanol was added to the washed precipitate and this mixture was heated and refluxed for 1 hour. After cooling to 20-25° C., the precipitate was filtered off, washed with 100 ml ethanol and dried at 50° C. under vacuum during 16 hours. Yield: 80.5 g of 4-[(1,4-dihydro-4-oxo-2-pyrimidinyl)amino]benzonitrile (75.9% yield).

The invention claimed is:

1. A process for preparing a compound of formula (I)

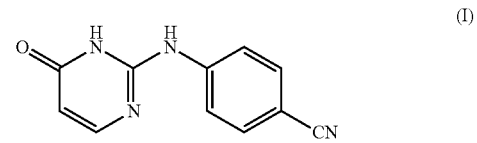 [SMILES: N#Cc1ccc(Nc2nccc(=O)[nH]2)cc1]

wherein the compound of formula (I) is prepared by dealkoxycarbonylating a 4-oxo-1,6-dihydro-pyrimidinyl carboxylic acid ester of formula (II):

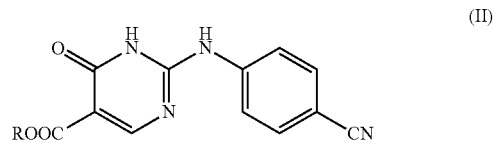

wherein R is $C_{1-4}$alkyl.

2. A process for preparing a compound of formula (I), as defined in claim 1, wherein the compound of formula (I) is prepared by condensing the guanidine of formula (III) with an alkoxymethylene malonic acid ester of formula (IV), thus obtaining an intermediate (II), which is dealkoxycarbonylated to obtain the desired end product of formula (I), as outlined in the following reaction scheme, wherein each R, independently from the other radicals R, is $C_{1-4}$alkyl:

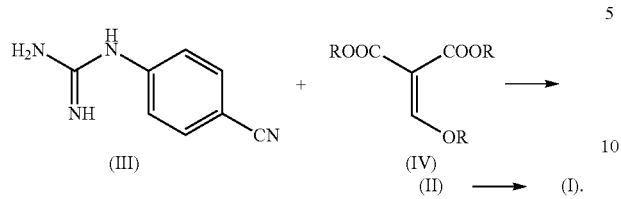

3. A process according to claim 2 wherein the conversion from (III) over (II) to obtain (I) is conducted in a one-pot reaction, without isolation of intermediate (II).

4. A process according to claim 1 wherein R is methyl or ethyl.

5. A process according to claim 1 wherein the process is conducted in the presence of a salt.

6. A process according to claim 5 wherein the salt is represented by formula MX wherein M is a metal or ammonium or substituted ammonium, and X is an anion having nucleophilic properties.

7. A process according to claim 6 wherein M is an alkali metal, ammonium or substituted ammonium and X is a halide, cyanide or $C_{1-4}$alkylcarboxylate.

8. A process according to claim 1 wherein the process is conducted in a dipolar aprotic solvent.

9. A process according to claim 8 wherein the solvent is selected from dimethylformamide (DMF), dimethylacetamide (DMA), hexamethylphosphoric acid triamide (HMPT), N-methylpyrrolidone (NMP), dimethylsulfoxide (DMSO) and acetonitrile.

10. A process according to claim 1 wherein at the end of the dealkoxycarbonylation step an acid is added to the reaction mixture.

11. The process according to claim 6, wherein M is an alkali metal and X is $C_{1-4}$alkylcarboxylate.

12. The process according to claim 10, wherein the acid is an alkylcarbonic acid.

13. The process according to claim 12 wherein the acid is $C_{1-4}$alkylcarbonic acid.

14. The process according to claim 13 wherein the acid is acetic acid.

15. The process according to claim 5 wherein the salt is sodium acetate.

16. The process according to claim 9 wherein the solvent is N-methylpyrrolidone.

17. A process to prepare (E)-4-[[4-[[4-(2-cyanoethenyl)-2,6-dimethylphenyl]-amino]-2-pyrimidinyl]-amino]-benzonitrile, wherein the process encompasses a process for preparing a compound of formula (I)

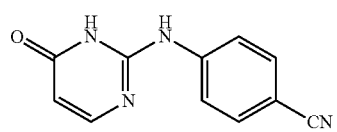

wherein the compound of formula (I) is prepared by dealkoxycarbonylating a 4-oxo-1,6-dihydro-pyrimidinyl carboxylic acid ester of formula (II):

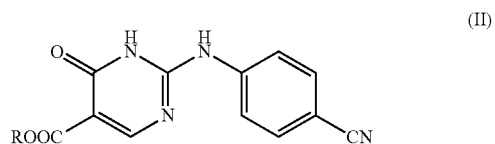

wherein R is $C_{1-4}$alkyl;

followed by halogenation of the obtained compound of formula (I) resulting in a compound of formula (C);

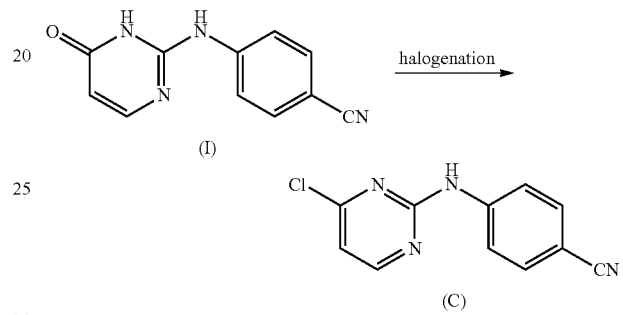

followed by coupling (E)-4-amino-3,5-dimethylcinnamonitrile (compound of formula B) with the obtained compound of formula (C) to give (E)-4-[[4-[[4-(2-cyanoethenyl)-2,6-dimethylphenyl]-amino]-2-pyrimidinyl]-amino]-benzonitrile (compound of formula A)

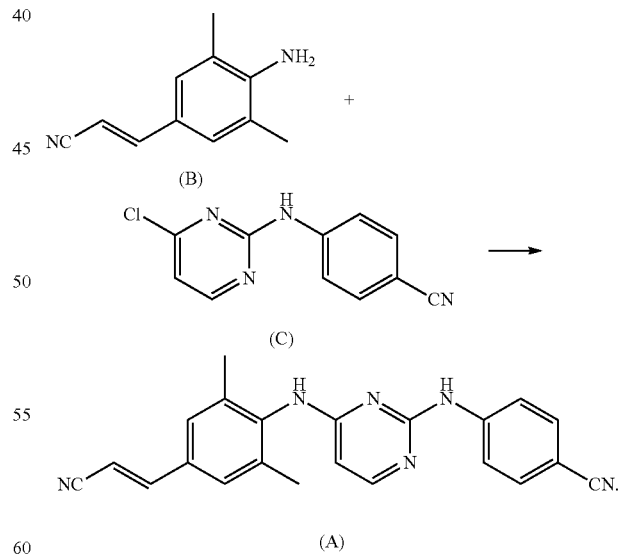

* * * * *